United States Patent
Hayashi (10) Patent No.: US 9,639,931 B2
(45) Date of Patent: May 2, 2017

(54) RADIATION IMAGE PROCESSING APPARATUS AND CONTROL METHOD FOR THE SAME

(71) Applicant: CANON KABUSHIKI KAISHA, Tokyo (JP)

(72) Inventor: Akinori Hayashi, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/661,108

(22) Filed: Mar. 18, 2015

(65) Prior Publication Data

US 2015/0279028 A1 Oct. 1, 2015

(30) Foreign Application Priority Data

Mar. 28, 2014 (JP) ................................ 2014-070078

(51) Int. Cl.
*G06K 9/00* (2006.01)
*G06T 7/00* (2017.01)
*G06F 19/00* (2011.01)

(52) U.S. Cl.
CPC .......... *G06T 7/0012* (2013.01); *G06F 19/321* (2013.01); *G06T 2207/10116* (2013.01)

(58) Field of Classification Search
None
See application file for complete search history.

(56) References Cited

U.S. PATENT DOCUMENTS

2013/0305138 A1* 11/2013 Gicovate .............. G06F 19/321
715/234
2014/0072191 A1* 3/2014 Liang ................... G06T 7/0012
382/128

FOREIGN PATENT DOCUMENTS

JP 2009-261541 11/2009

* cited by examiner

*Primary Examiner* — Atiba O Fitzpatrick
(74) *Attorney, Agent, or Firm* — Fitzpatrick, Cella, Harper & Scinto (57) ABSTRACT

A radiation image processing apparatus comprises a storage unit that stores part information with which an imaging region and an extraction size of a radiation image are associated, a recognizing unit that recognizes a region of interest from a radiation image based on an image region associated with designated part information, and an arrangement unit that arranges an extraction area of an extraction size associated with the designated part information on the radiation image in accordance with the region of interest recognized by the recognizing unit.

12 Claims, 11 Drawing Sheets

FIG. 3

| PART INFORMATION NAME | IMAGING PART | EXTRACTION SIZE | EXTRACTION CONDITION |
|---|---|---|---|
| PART INFORMATION A | FRONT OF CHEST | 17×14 INCHES | EXTRACT AREA OBTAINED BY EXTENDING REGION OF INTEREST 1 cm UPWARD FROM UPPER EDGE |
| PART INFORMATION B | SIDE OF CHEST | 14×17 INCHES | EXTRACT AREA UNIFORMLY FROM LEFT AND RIGHT EDGES OF REGION OF INTEREST |
| PART INFORMATION C | SIDE OF CHEST | 14×14 INCHES | EXTRACT AREA OBTAINED BY EXTENDING REGION OF INTEREST 1 cm DOWNWARD FROM LOWER EDGE |

RADIATION IMAGE PROCESSING APPARATUS AND CONTROL METHOD FOR THE SAME

BACKGROUND OF THE INVENTION

Field of the Invention

The present invention relates to a radiation image processing apparatus and a control method for the same.

Description of the Related Art

There has been a growing trend to implement more efficient and faster examination by saving and transmitting medical image information of patients generated in hospitals upon digitizing the information. For this reason, in the field of radiographic imaging as well, a radiographic imaging system has been increasingly used, which uses a radiation detector such as an FPD (Flat Panel Detector) in place of a conventional screen/film system and outputs digital data.

In a radiographic imaging system like that described above, the size of an obtained image depends on the size of a radiation detector such an FPD used for imaging, and hence an unnecessary area for diagnosis is sometimes generated in an obtained image. For this reason, it is a general practice for a user such as a doctor or technician to extract a necessary area for diagnosis for every imaging operation and send the extracted area to a PACS (Picture Archiving and Communication System) or the like. It is also a practice to print, on films, the images sent to the PACS and perform quality assurance for images on a display.

For the purpose of supporting extraction of an area from an obtained image, there has been proposed a system which detects a necessary area (region of interest) for diagnosis and decides an extraction area based on the resultant information. Japanese Patent Laid-Open No. 2009-261541 (to be referred to as patent literature 1 hereinafter) discloses a radiographic imaging system which detects a region of interest from an obtained image and sets, as an extraction area, a surrounding area extending from the detected region of interest by an amount corresponding to a predetermined number of pixels.

The radiographic imaging system disclosed in patent literature 1, however, decides an extraction area with reference to a detected region of interest, and hence an extraction area changes in size depending on the size of a detected region of interest even if the same region is imaged. For example, even if the same region of the same patient is imaged, different extraction regions are obtained from different detected regions of interest, and images extracted in different sizes are sent to a PACS. In general, commercially available films have predetermined sizes such as 14×17 inches, 14×14 inches, and 10×12 inches. It is preferable to print images obtained by imaging the same region of the same patient on films of the same size. According to the radiographic imaging system disclosed in patent literature 1, however, images sent to a PACS may be printed on films of different sizes.

SUMMARY OF THE INVENTION

An embodiment of the present invention provides a radiographic imaging unit which can properly extract an image containing a necessary portion from a radiation image and a control method for the unit.

According to one aspect of the present invention, there is provided a radiation image processing apparatus comprising: a storage unit configured to store part information with which an imaging region and an extraction size of a radiation image are associated; a recognizing unit configured to recognize a region of interest from a radiation image based on an image region associated with designated part information; and an arrangement unit configured to arrange an extraction area of an extraction size associated with the designated part information on the radiation image in accordance with the region of interest recognized by the recognizing unit.

Furthermore, according to one aspect of the present invention, there is provided a control method for a radiation image processing apparatus, the method comprising: an obtaining step of obtaining designated part information from a storage unit configured to store a plurality of pieces of part information with which image regions and extraction sizes of radiation images are associated; a recognizing step of recognizing a region of interest from a radiation image based on an imaging region associated with part information obtained in the obtaining step; and an arrangement step of arranging an extraction area of an extraction size associated with the obtained part information on the radiation image in accordance with the region of interest recognized in the recognizing step.

Further features of the present invention will become apparent from the following description of exemplary embodiments (with reference to the attached drawings).

DESCRIPTION OF THE EMBODIMENTS

The preferred embodiments of the present invention will be described below with reference to the accompanying drawings.

<First Embodiment>

Figure 1:
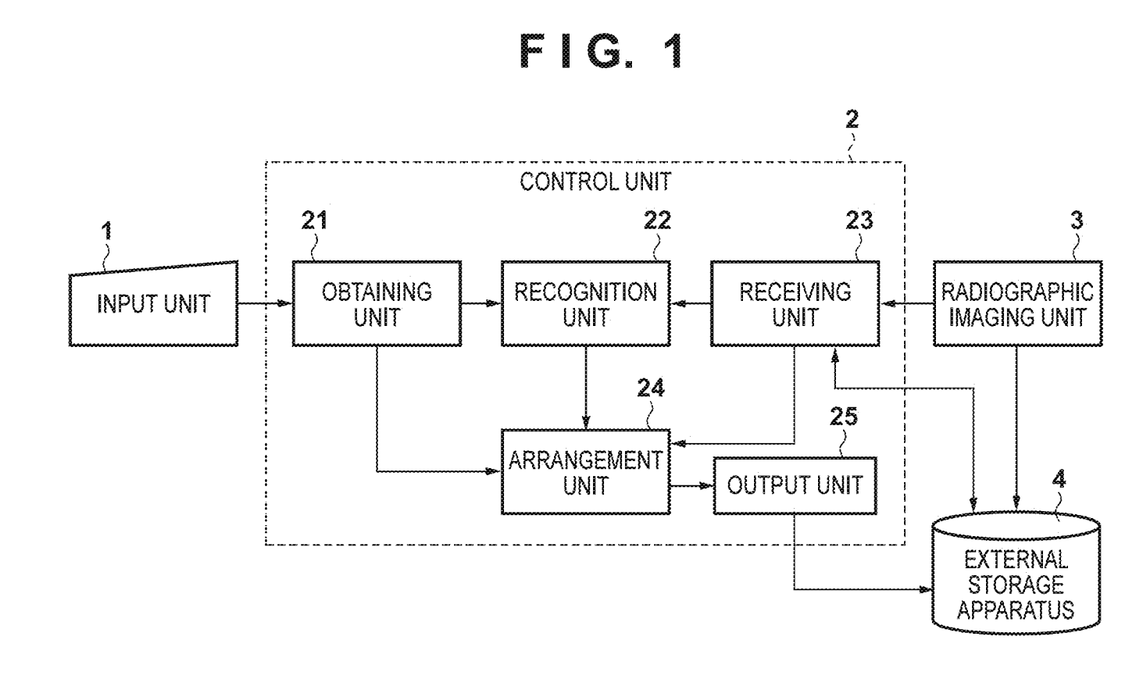
FIG. 1 is a block diagram showing an example of the functional arrangement of a radiographic imaging system according to the first embodiment.

FIG. 1 is a block diagram showing the functional arrangement of a radiographic imaging system according to the first embodiment. Referring to FIG. 1, an input unit 1 includes a mouse, a keyboard, and a trackball and accepts an instruction input from a user such as a doctor or radiology technician. A control unit 2 performs various types of control on the radiographic imaging system. As will be described later with reference to FIG. 2, the control unit 2 includes a microprocessor (CPU), and executes various types of processing including radiation image processing (to be described later) by causing the microprocessor to execute control programs stored in a memory. A radiographic imaging unit 3 includes a radiation source, a radiation detector, and an image display unit, and obtains an obtained image by radiation such as X-rays. An external storage apparatus 4 stores the radiation images obtained by the radiographic imaging unit 3 and the images extracted by the control unit 2.

Figure 2:
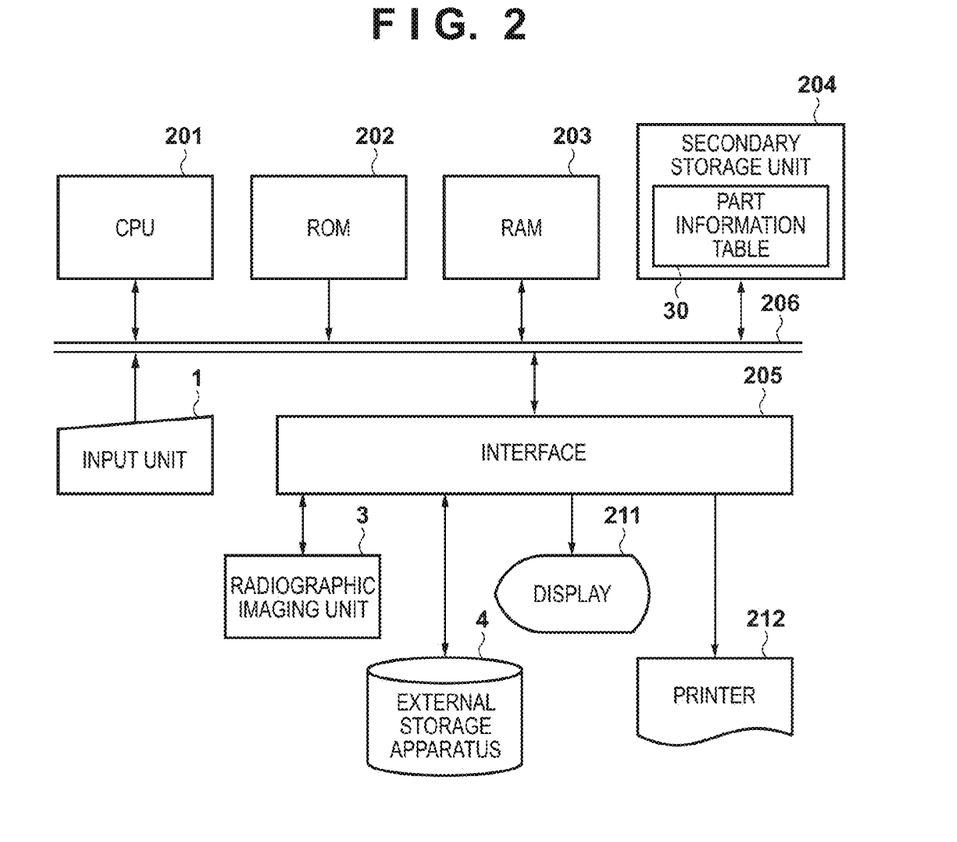
FIG. 2 is a block diagram showing an example of the hardware arrangement of a control unit according to the first embodiment.

FIG. 2 is a block diagram for explaining the arrangement of the control unit 2. A CPU 201 executes various types of control by executing programs stored in a ROM 202 and programs loaded into a RAM 203. A secondary storage unit 204 is formed from, for example, a hard disk, and stores programs to be loaded into the RAM 203 and executed by the CPU 201 and the radiation images received from the radiographic imaging unit 3. An interface 205 connects external apparatuses such as the radiographic imaging unit 3, the external storage apparatus 4, a display 211, and a printer 212 to the control unit 2. A bus 206 communicably connects the above units to each other.

The respective units of the control unit 2 shown in FIG. 1 are implemented by making the CPU 201 execute predetermined programs. Note that all or some of the units of the control unit 2 may be implemented by dedicated hardware. An obtaining unit 21 obtains part information in accordance with an instruction from the input unit 1. Part information is held, as a part information table 30 having a data arrangement like that shown in, for example, FIG. 3, in the secondary storage unit 204, as shown in, for example, FIG. 2. The user can designate desired part information from a plurality of pieces of part information (pieces of part information A to C in the case shown in FIG. 3) via a predetermined user interface (for example, a combination of a GUI and a touch panel) provided by the input unit 1. In each piece of part information, a part information name 31, an imaging part 32 as a radiographic imaging target, an extraction size 33 indicating the size of an area to be extracted from a radiation image, and an extraction condition 34 for the extraction of an area from a radiation image are associated with each other. The user can designate desired part information by designating a part information name from the input unit 1. The obtaining unit 21 obtains part information designated via the input unit 1 from the part information table 30, and provides the information to a recognition unit 22 and an arrangement unit 24.

A receiving unit 23 receives a radiation image from the radiographic imaging unit 3 via the interface 205, and holds it in the secondary storage unit 204. Note that the receiving unit 23 may receive a radiation image from the external storage apparatus 4. The recognition unit 22 recognizes a region of interest in the radiation image received by the receiving unit 23 based on an imaging part 32 indicated by the part information obtained by the obtaining unit 21. The arrangement unit 24 arranges an extraction area on the radiation image in accordance with an extraction size 33 and an extraction condition 34 which are indicated by the part information obtained by the obtaining unit 21. An output unit 25 outputs a radiation image in the extraction area arranged by the arrangement unit 24 to an external apparatus such as the display 211, the printer 212, or the external storage apparatus 4.

Figure 3:
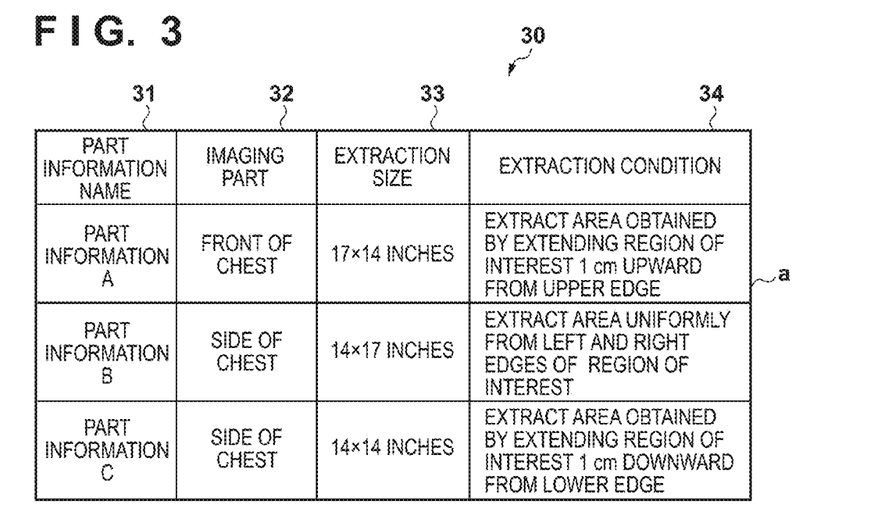
FIG. 3 is a view showing an example of the data arrangement of a part information table.

In the part information table 30 shown in FIG. 3, part information is formed from a combination of the part information name 31, the imaging part 32, the extraction size 33, and the extraction condition 34. The part information name 31 indicates the name arbitrarily assigned to the part information. The imaging part 32 is information indicating a part of an object, for example, the front of the chest, the side of the chest, the abdominal region, or the head region, which is information to be referred to when the recognition unit 22 extracts a region of interest. That is, the recognition unit 22 recognizes a region of interest by using a processing parameter corresponding to a designated imaging part. A region of interest in this case may be, for example, a lung field region in an object area when an imaging part is the front of the chest, or an overall object area when an imaging part is the head region. That is, area recognition criterion may differ for each imaging part. It is possible to change part information by changing the contents of the imaging part 32. In addition, imaging parts are not limited to general imaging parts such as the front of the chest and the side of the chest, and the user may arbitrarily prepare an imaging part (in this case, it is necessary to associate in advance a processing parameter for the recognition of a region of interest with the prepared imaging part). The extraction size 33 is information indicating the size of an extraction area. It is possible to change the part information by changing an extraction size. In this case, the extraction size is one selected from 14×14 inches, 14×17 inches, and 17×14 inches, which are film sizes. However, the extraction size to be used is not limited to this and may be the size arbitrarily defined by the user.

The extraction condition 34 indicates an arrangement condition for an extraction area. It is possible to change the part information by changing the extraction condition 34. In the case shown in FIG. 3, in part information A, as the extraction condition 34, there is set a condition that the area obtained by extending a region of interest 1 cm upward from the upper edge should be extracted. If, therefore, part information A is designated, the arrangement unit 24 arranges an extraction area of the size (17×14 inches) designated by the extraction size 33 so as to include the area obtained by extending the region of interest, recognized by the recognition unit 22, 1 cm upward from the upper edge.

Figure 4:
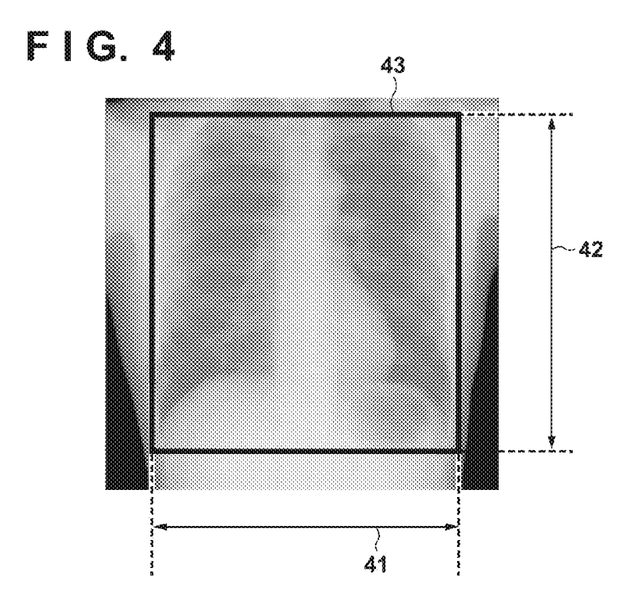
FIG. 4 is a view showing an example of recognition of a region of interest.

FIG. 4 shows an example of the region of interest recognized by the recognition unit 22 with respect to a radiation image. When the imaging part 32 is the front of the chest, the recognition unit 22 recognizes the left and right edges of the lung fields from the radiation image and sets them as the left and right edges of a region of interest. Likewise, the recognition unit 22 sets, as the upper and lower edges of the region of interest, the upper and lower edges of the lung fields obtained in the radiation image of the front of the chest. As a result, the recognition unit 22 recognizes a region of interest 43 indicated by a horizontal double-headed arrow 41 and a vertical double-headed arrow 42.

Figure 12:
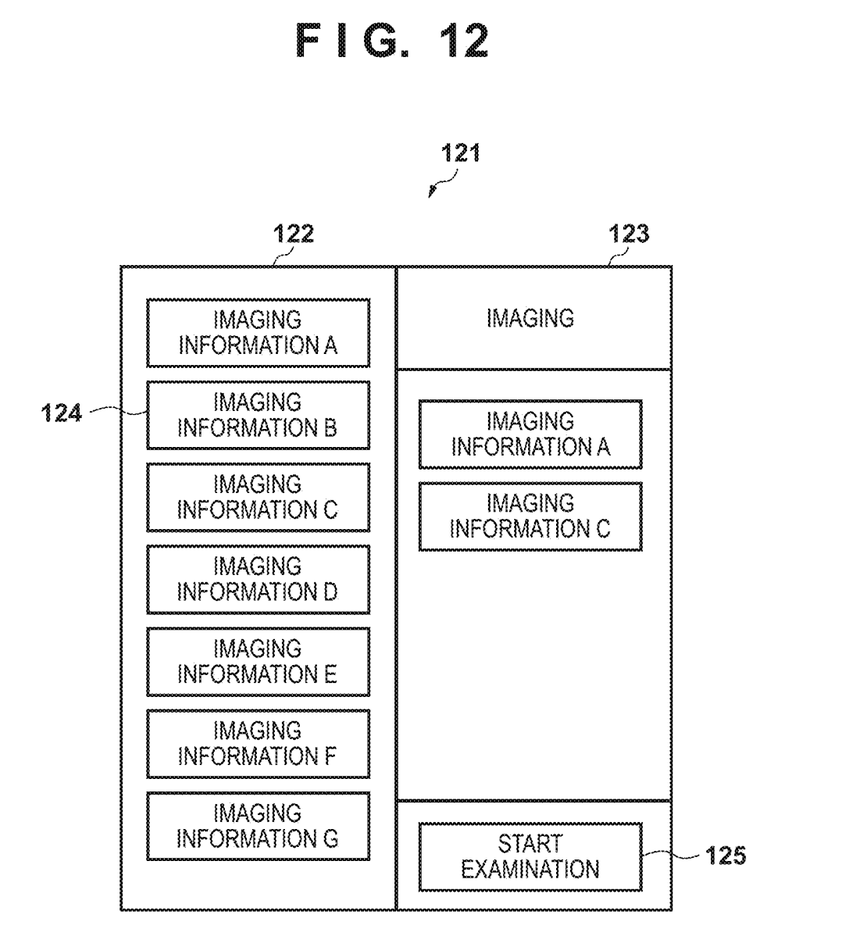
FIG. 12 is a view for explaining a GUI example for imaging information selection according to the first embodiment.

FIG. 12 shows an example of the GUI provided for the selection of part information for imaging by the user in the radiographic imaging system according to the first embodiment. A screen 121 includes a part information list screen 122 and a selected part information screen 123. When the user selects a part information name 124 displayed on the part information list screen 122, the part information name 124 is displayed as selected information on the selected part information screen 123. When the user presses an examination start button 125, an examination is started under the condition of the selected part information name 124. The part information name 124 represents the part information name 31. If, for example, the user selects part information A on the part information list screen 122 and presses the examination start button 125, it indicates that an examination is performed under the condition set when the part information name 31 is imaging information A.

Figure 5:
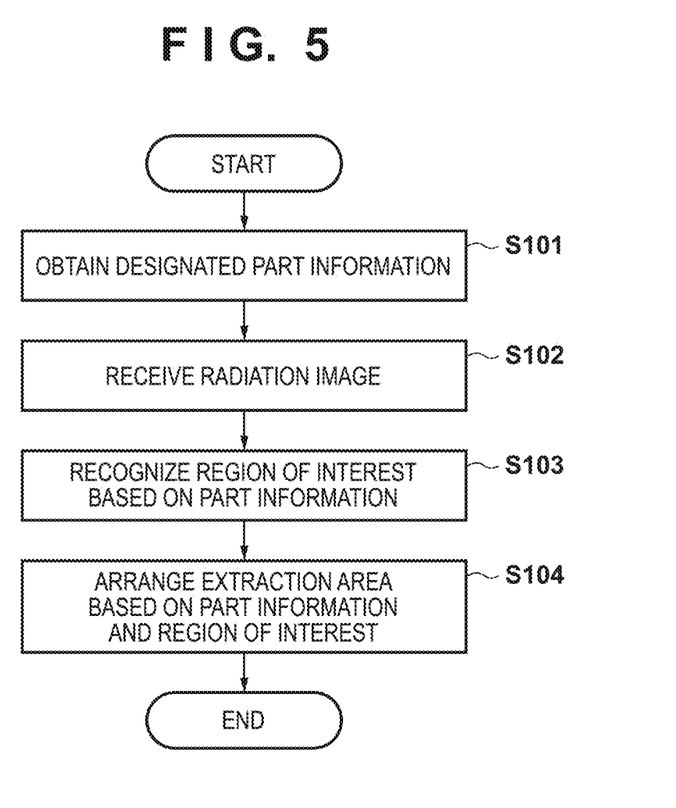
FIG. 5 is a flowchart for explaining arrangement processing for an extraction area according to the first embodiment.

FIG. 5 is a flowchart for explaining radiation image processing (image extraction processing) executed by the control unit 2 in the radiographic imaging system according to the first embodiment. In step S101, the obtaining unit 21 obtains the part information designated by the user via the input unit 1 from the part information table 30. If, for example, the user designates part information A via the input unit 1, the obtaining unit 21 obtains, from the part information table 30, part information including "front chest" as an imaging part, "17×14 inches" as an extraction size, and "extract area obtained by extending region of interest 1 cm upward from upper edge" as an extraction condition.

In step S102, the receiving unit 23 receives a radiation image from the radiographic imaging unit 3. As described above, the receiving unit 23 may receive a radiation image stored in the external storage apparatus 4. In step S103, the recognition unit 22 recognizes a region of interest from the radiation image based on the imaging part contained in the part information obtained by the obtaining unit 21 and the radiation image received by the receiving unit 23. If, for example, the imaging part is the front of the chest, the recognition unit 22 recognizes the lung fields of the front of the chest as a region of interest.

In step S104, the arrangement unit 24 arranges an extraction area on the radiation image received by the receiving unit 23 based on the extraction size and extraction condition indicated by the part information designated by the obtaining unit 21 and the region of interest recognized by the recognition unit 22. The arrangement unit 24 arranges an area having the extraction size so as to enclose the recognized region of interest, as exemplified below.

[Arrangement Example 1]

Figure 6A:
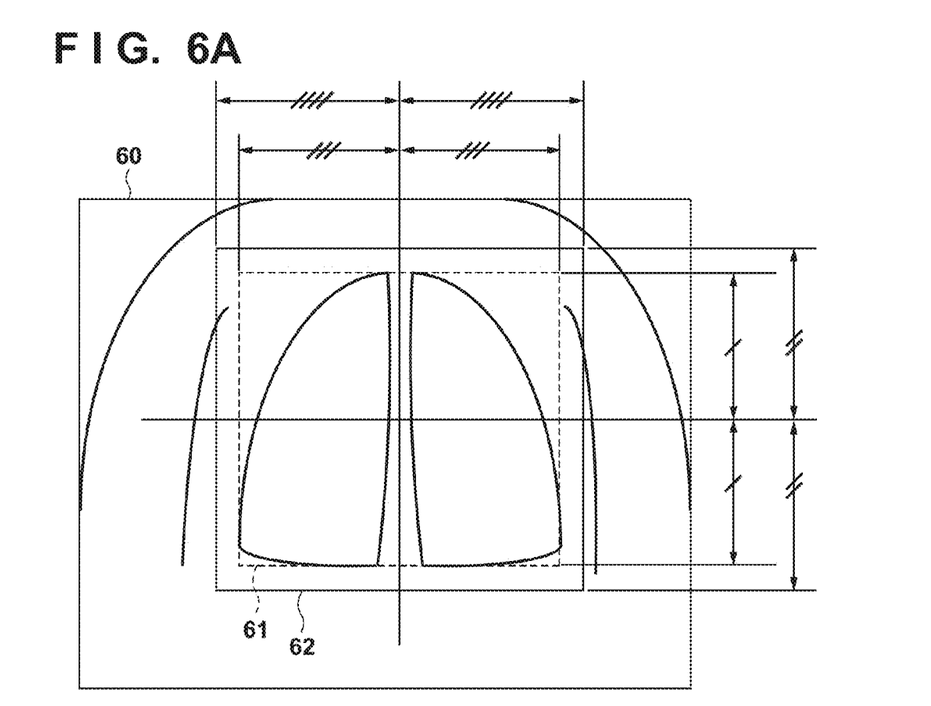
FIGS. 6A and 6B are views for explaining an example of arrangement processing for an extraction area according to the first embodiment.
Figure 6B:
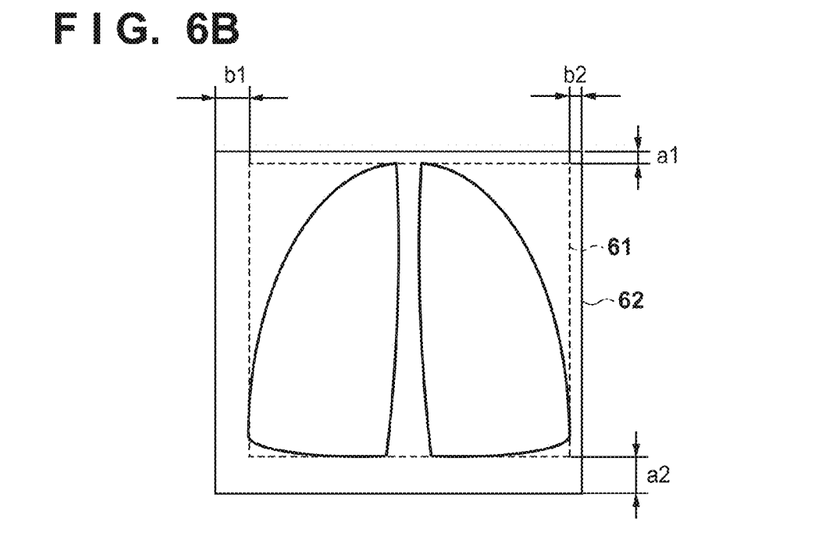

The recognition unit 22 basically arranges an extraction area such that the center of a region of interest coincides with the center of the area having an extraction size, and changes the arrangement of the extraction area in accordance with the extraction condition associated with part information. FIGS. 6A and 6B are views for explaining an extraction area arrangement method performed by the arrangement unit 24. If no condition is designated by the extraction condition 34 in the part information, the arrangement unit 24 arranges an extraction area such that the center of a region of interest 61 recognized in a radiation image 60 coincides with the center of an extraction area 62, as shown in FIG. 6A.

[Arrangement Example 2]

If the extraction condition defined includes the ratio between the distance between the upper and lower edges of the region of interest 61 and the distance between the upper and lower edges of the extraction area 62 and the ratio between the distance between the left and right edges of the region of interest 61 and the distance between the left and right edges of the extraction area 62, an extraction area is arranged as shown in FIG. 6B. In this case, the extraction condition defined includes the ratio between a1 and a2 and the ratio between b1 and b2 shown in FIG. 6B. Note that if the center of the region of interest 61 coincides with the center of the extraction area 62 as shown in FIG. 6A, it equivalently indicates that the ratio between a1 and a2 and the ratio between b1 and b2 each are set to 1.

[Arrangement Example 3]

Figure 7A:
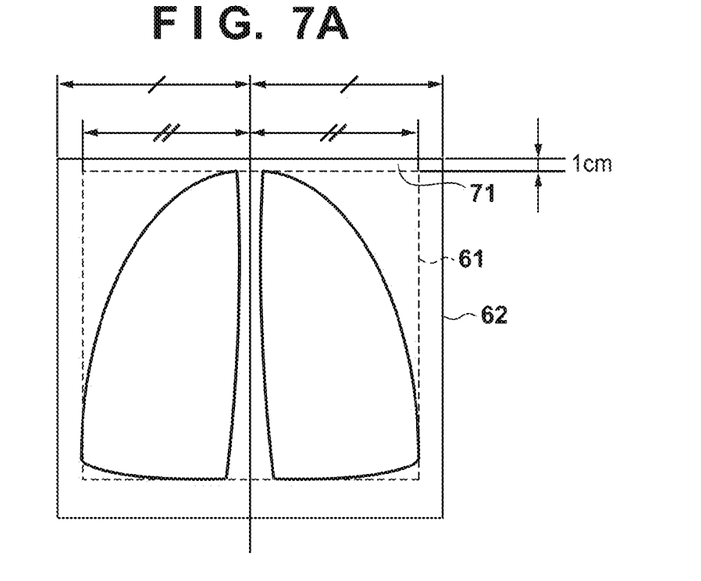
FIGS. 7A and 7B are views for explaining an example of arrangement processing for an extraction area according to the first embodiment.

The next description is the arrangement of an extraction area when the condition "extract area obtained by extending region of interest 1 cm upward from upper edge" is set as indicated by the extraction condition 34 of part information A. In this case, the arrangement unit 24 arranges an extraction area so as to enclose a target area obtained by adding an added area designated by the extraction condition (an area having a height of 1 cm and the same width as that of the region of interest) to the region of interest. If, for example, the extraction condition 34 of part information A is set, the arrangement unit 24 arranges the extraction area 62 such that an edge portion of the target area constituted by the region of interest 61 and the added area 71, coincides with an edge portion of the extraction area, as shown in FIG. 7A. In other words, the arrangement unit 24 arranges the extraction area 62 such that the position 1 cm above the upper edge of the region of interest 61 coincides with the upper edge of the extraction area.

Figure 7B:
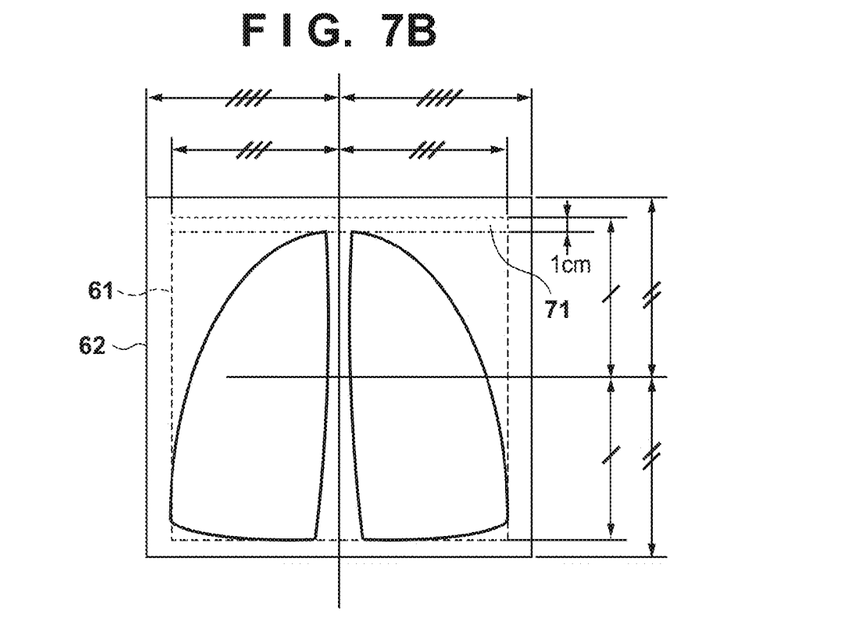

Note that the extraction method to be used when the extraction condition "extract area obtained by extending region of interest 1 cm upward from upper edge" is not limited the method shown in FIG. 7A. For example, as shown in FIG. 7B, the arrangement unit 24 may arrange the extraction area 62 such that the center of the target area obtained by adding an added area 71 having a width of 1 cm to the upper edge of the region of interest 61 coincides with the center of the extraction area. In addition, an extraction area may be arranged by deciding the positional relationship between the extraction area and a target area by using ratios like those described with reference to [Arrangement Example 2] (FIG. 6B).

The above description has exemplified the case in which an added area having a designated height is added to an upper edge of a region of interest. It is, however, obvious that this embodiment can be executed in a similar manner even when an area is added to the lower, left, or right edge of a region of interest. As described above, if an extraction condition defines an added area to be ensured around the region of interest recognized by the recognition unit 22, the arrangement unit 24 arranges an extraction area so as to enclose the target area obtained by adding the added area to the region of interest.

[Arrangement Example 4]

Figure 8A:
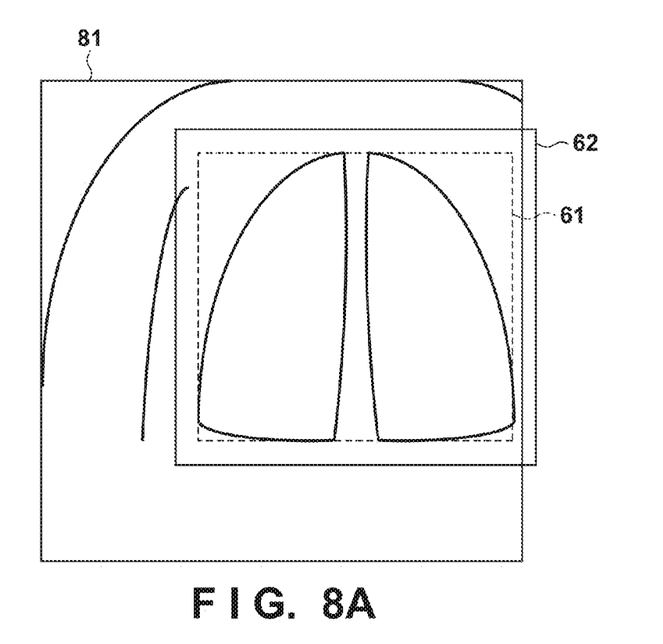
FIGS. 8A to 8C are views for explaining an example of arrangement processing for an extraction area according to the first embodiment.
Figure 8B:
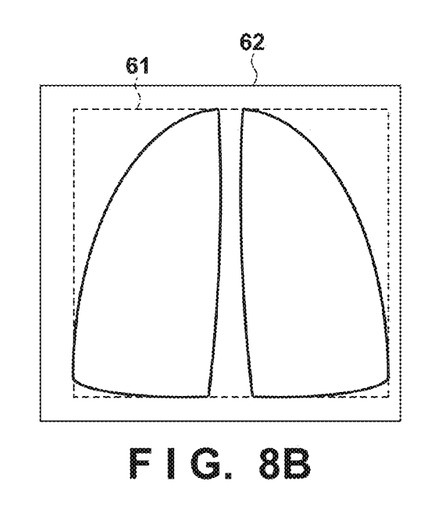

The following will exemplify a case in which an extraction area protrudes outside a radiation image as a result of arranging the extraction area based on the region of interest recognized by the recognition unit 22 by the above method. A case in which part of the extraction area 62 protrudes outside a radiation image 81 as a result of arranging the extraction area 62 based on the region of interest 61, as shown in, for example, FIG. 8A, will be described below. In this case, for example, the arrangement unit 24 adjusts an arrangement position so as to eliminate the protruding portion of the extraction area 62. For example, as shown in FIG. 8B, the arrangement unit 24 performs extraction by moving the extraction area 62 such that the protruding right edge portion of the extraction area 62 coincides with the right edge portion of the radiation image 81.

Figure 8C:
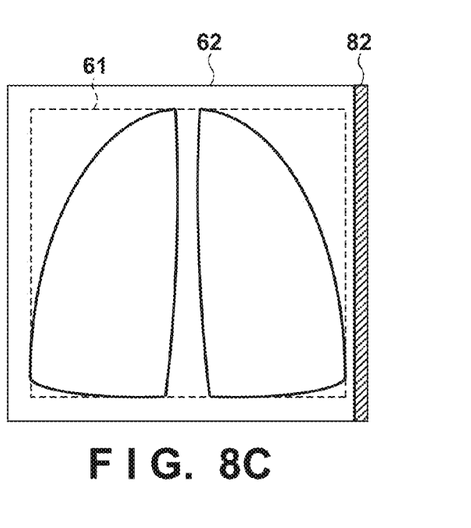

Alternatively, as shown in FIG. 8C, the arrangement unit 24 adds an image 82 having a predetermined luminance (for example, black) to the protruding portion of the extraction area 62. In this case, the output unit 25 outputs an image obtained by adding the image 82 to the image of the overlapping portion between the radiation image 81 and the extraction area 62.

[Arrangement Example 5]

Note that if the region of interest recognized by the recognition unit 22 is larger than the extraction size defined in part information, one of the following three methods is used:

extracting an extraction area such that the center of a region of interest coincides with the center of the extraction area;

setting a region of interest as an extraction area; and setting the range obtained by adding an area to the circumference of a region of interest (for example, each of the four sides of the region of interest) as a new extraction area.

As described above, according to the first embodiment, when the same part information is designated, if a recognized region of interest is smaller than the extraction size defined by the part information, an extraction area of the same size is arranged on a radiation image regardless of the size of the region of interest. Therefore, for example, images of the same size can be obtained by imaging the same region of the same patient. This makes it possible, for example, to print these images on films of the same size, thereby obtaining radiation images which can be used more easily for diagnosis.

In addition, for example, when the front of the chest is imaged, an important area at the time of diagnosis is mainly the lung field region. However, a doctor or technician extracts images including the collarbone, the scapula, and the diaphragm and save them. That is, extracted images do not exclusively include only regions of interest. On the other hand, with regard to an obtained image of a joint or the like as an imaging part, importance is attached to a region of interest, and a peripheral image is rarely extracted. The radiographic imaging system according to this embodiment automatically extracts an area including a region of interest and its peripheral portion in accordance with the region of interest recognized in this manner, and hence reduces the operation load on the user.

<Second Embodiment>

The first embodiment has exemplified the arrangement in which one extraction size is associated with each piece of part information. According to the second embodiment, two or more extraction sizes are permitted to be associated with one piece of part information.

Figure 9:
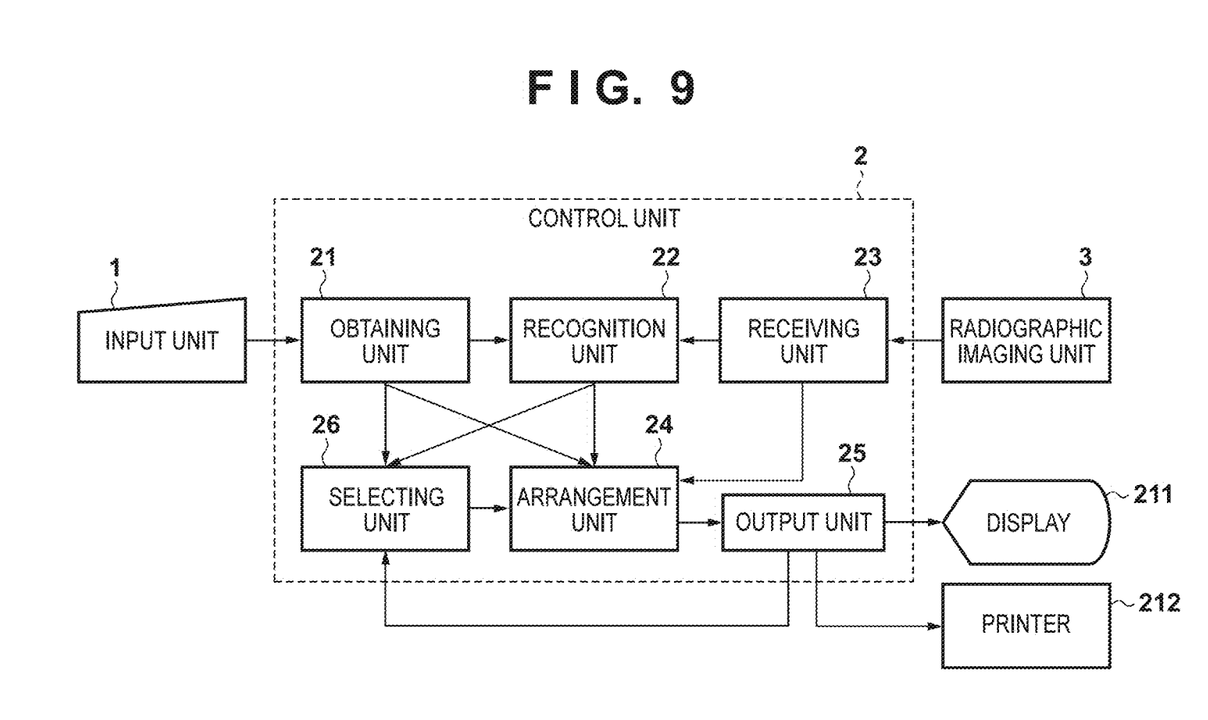
FIG. 9 is a block diagram showing an example of the functional arrangement of a radiographic imaging unit according to the second embodiment.

FIG. 9 is a block diagram for explaining the functional arrangement of a radiographic imaging system according to the second embodiment. The same reference numerals as in FIG. 1 denote the same components in FIG. 9. A display 211 and a printer 212 are connected to an output unit 25. The output unit 25 outputs a radiation image of the extraction area arranged by an arrangement unit 24. A selecting unit 26 selects one of a plurality of extraction areas attached to part information obtained by an obtaining unit 21 based on the region of interest recognized by the recognition unit 22 and the type of output destination of the radiation image from the output unit 25. As output destinations, this embodiment uses, for example, the display 211 (viewer) and the printer 212 (film). The arrangement unit 24 arranges the area of the extraction size selected by the selecting unit 26 on the radiation image received by a receiving unit 23 based on the part information obtained by the obtaining unit 21 and the region of interest recognized by the recognition unit 22.

Figure 10:
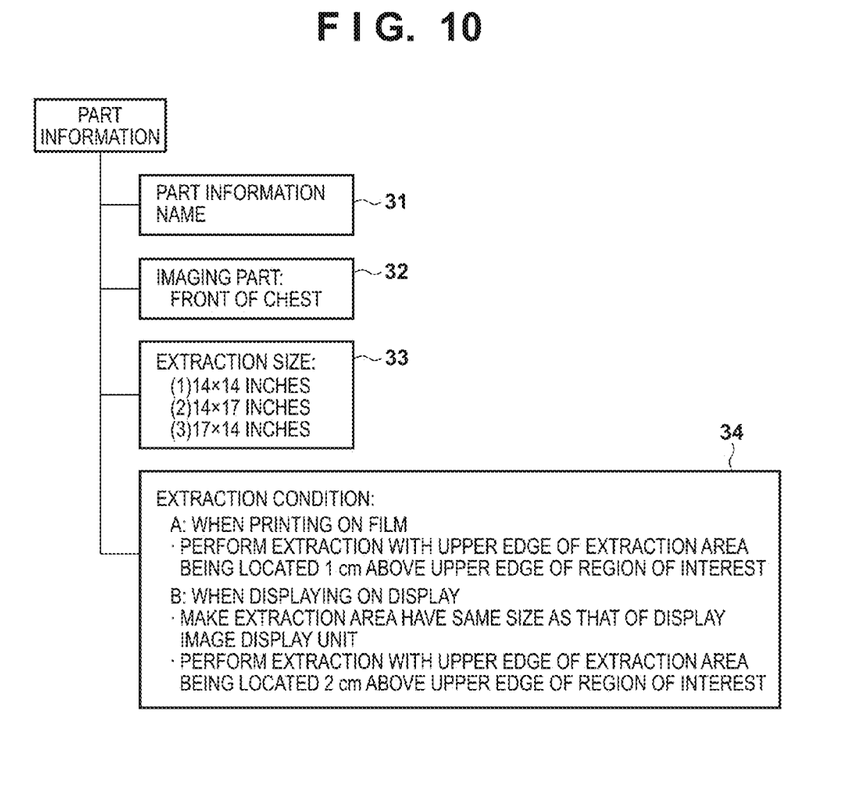
FIG. 10 is a view for explaining the data arrangement of part information according to the second embodiment.

FIG. 10 is a view for explaining an example of the data arrangement of part information registered in a part information table 30 according to the second embodiment. As in the first embodiment, part information according to the second embodiment includes a part information name 31, an imaging part 32, an extraction size 33, and an extraction condition 34. According to the second embodiment, the extraction size 33 includes a plurality of extraction sizes. It is possible to change the part information by changing these extraction sizes. In addition, extraction sizes may be those of areas arbitrarily created by the user.

The extraction condition 34 includes a plurality of extraction conditions prepared for each output designation. It is possible to change the part information by changing extraction conditions. In addition, according to this embodiment, extraction conditions are set for a case in which the printer 212 prints an image on a film and a case in which the display 211 performs screen display. However, this is not exhaustive. For example, it is possible to add extraction conditions for PACS transfer. In addition, an extraction area size may be designated in accordance with an output destination.

Figure 11:
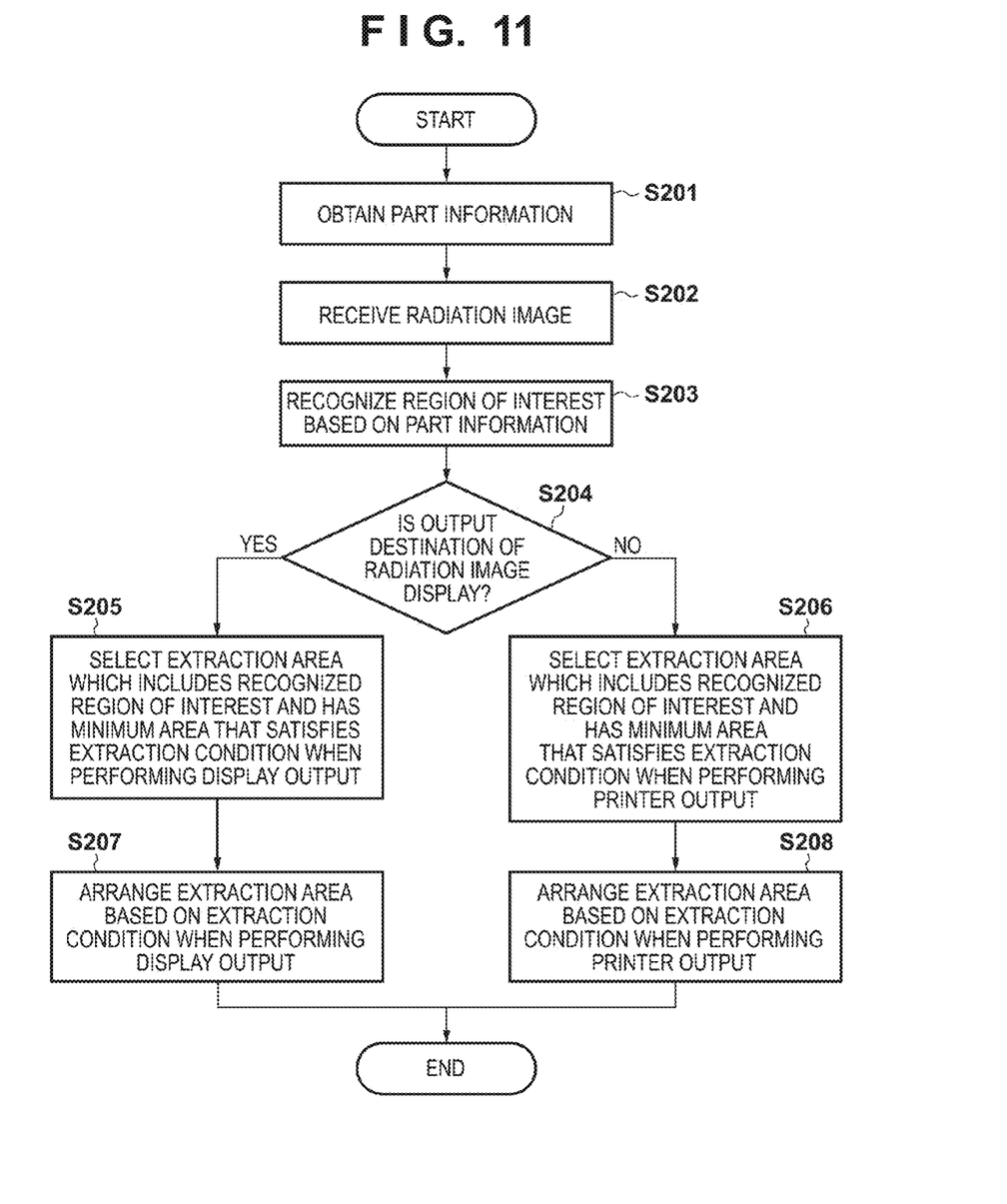
FIG. 11 is a flowchart for explaining arrangement processing for an extraction area according to the second embodiment.

FIG. 11 is a flowchart for explaining radiation image processing (image extraction processing) executed by the control unit 2 in the radiographic imaging system according to the second embodiment. Note that the processing from step S201 to step S203 is the same as that in the first embodiment (steps S101 to S103 in FIG. 5).

In steps S204 to S206, the selecting unit 26 selects one of a plurality of extraction sizes based on the output destination (the display 211 or the printer 212 in this embodiment) of a radiation image from the output unit 25 and the region of interest recognized by a recognition unit 22. That is, in step S204, the selecting unit 26 determines whether the output destination of the radiation image is the display 211 or the printer 212. If the destination is the display 211, the process advances to step S205. The selecting unit 26 selects a size corresponding to the minimum area that encloses the region of interest recognized by the recognition unit 22 out of the extraction sizes that can be used for display output. In step S207, the arrangement unit 24 arranges an extraction area of the selected extraction size on the radiation image in accordance with an extraction condition for the display 211 (extraction condition B in FIG. 10).

On the other hand, if it is determined in step S204 that the output destination is the printer 212, the process advances to step S206. The selecting unit 26 selects a size corresponding to the minimum area that encloses the region of interest recognized by the recognition unit 22 out of the extraction sizes that can be used for printer output. In step S208, the arrangement unit 24 arranges an extraction area of the selected extraction size on the radiation image in accordance with an extraction condition for the printer 212 (extraction condition A in FIG. 10). Note that if there is only one extraction size corresponding to the type of output destination, the extraction size is selected. In addition, if no extraction size selection method is set in an extraction condition, the selecting unit 26 selects an extraction size corresponding to the minimum area out of extraction sizes that enclose the overall region of interest or the overall target area.

Although the second embodiment has exemplified the display 211 and the printer 212 as output destinations of radiation images from the output unit 25, they are not exhaustive. In addition, obviously, as extraction area arrangement methods, for example, the arrangement methods described with reference to arrangement examples 1 to 5 in the first embodiment can be used.

As described above, according to the second embodiment, an extraction area can be properly arranged in accordance with an output destination. For example, the size (pixel count) of a commercially available image viewer such as a display is determined in advance. When, therefore, the image sent to a PACS is to be displayed on the image viewer, the image is displayed after being enlarged or reduced in accordance with the size of the image viewer. Assume that the operator continuously performs quality assurance for images of the same region of the same patient to check the progress of a lesion. In this case, if these images are extracted in different sizes, the images are displayed on the image viewer at different magnifications. When checking the progress of the lesion of the same patient, it is obvious that images to be displayed include the region of interest and have the same size (magnification). According to this embodiment, since it is possible to decide the size and arrangement position of an extraction area in accordance with an output destination, it is possible to output images to be displayed on the image viewer at a unified magnification. In addition, setting in advance an extraction size corresponding to the aspect ratio of the image viewer makes it possible to enlarge and display an image over the entire image viewer without changing the aspect ratio.

As has been described above, each embodiment provides a radiographic imaging unit which can properly extract an image including a necessary portion from a radiation image and a control method for the unit.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-070078, filed Mar. 28, 2014, which is hereby incorporated by reference herein in its entirety.

What is claimed is:

1. A radiation image processing apparatus comprising a processor implementing functions of:
    a storage unit configured to store a plurality of pieces of part information, each including an imaging part indicating a part of an object to be imaged and an extraction size of an extraction area on a radiation image;
    a recognizing unit configured to recognize a region of interest from a radiation image based on the imaging part included in designated part information among the plurality of pieces of part information; and
    an arrangement unit configured to arrange the extraction area with a predetermined extraction size in association with the designated part information on the radiation image in accordance with the region of interest recognized by said recognizing unit.

2. The apparatus according to claim 1, wherein said arrangement unit sets the overall region of interest recognized by said recognizing unit as a target area enclosed in the extraction area.

3. The apparatus according to claim 1, wherein an extraction condition is associated with the part information, and
    said arrangement unit arranges the extraction area on the radiation image so as to enclose the region of interest based on the region of interest recognized by said recognizing unit and the extraction condition.

4. The apparatus according to claim 3, wherein the extraction condition defines an added area to be ensured around a region of interest recognized by said recognizing unit, and
    said arrangement unit arranges the extraction area so as to enclose a target area obtained by adding the added area to the region of interest.

5. The apparatus according to claim 4, wherein said arrangement unit arranges the extraction area such that an edge portion, of edge portions of the target area, which is formed by the added area coincides with an edge portion of the extraction area.

6. The apparatus according to claim 1, wherein the part information includes a plurality of extraction sizes,
    the apparatus further comprises a selecting unit configured to select one of the plurality of extraction sizes for said arrangement unit based on the target area, and
    said selecting unit selecting an extraction size corresponding to a minimum area out of extraction sizes that enclose the target area.

7. The apparatus according to claim 2, wherein the part information includes a plurality of extraction sizes,
    the apparatus further comprises a selecting unit configured to select one of the plurality of extraction sizes for said arrangement unit based on the target area, and
    said selecting unit selecting one of the plurality of extraction sizes in accordance with a type of an apparatus as an output destination of the extraction area.

8. The apparatus according to claim 7, wherein if there are a plurality of extraction sizes corresponding to a plurality of types of apparatuses as output destinations of the extraction area, said selecting unit selects an extraction size corresponding to a minimum area that encloses the target area out of the extraction sizes.

9. The apparatus according to claim 1, wherein if the extraction area arranged on the radiation image protrudes from the radiation image, said arrangement unit adjusts a position of the extraction area such that an edge portion of the extraction area on a side where the extraction area protrudes coincides with an edge portion of the radiation image.

10. The apparatus according to claim 1, wherein if the extraction area arranged on the radiation image protrudes from the radiation image, said arrangement unit performs extraction upon adding an image having a predetermined luminance to a protruding portion.

11. A control method for a radiation image processing apparatus, the method comprising:
- obtaining designated part information from a storage unit configured to store a plurality of pieces of part information each including an imaging part indicating a part of an object to be imaged and an extraction size of an extraction area on a radiation image;
- recognizing a region of interest from the radiation image based on an imaging part included in the obtained part information; and
- arranging the extraction area with a predetermined extraction size in association with the obtained part information on the radiation image in accordance with the recognized region of interest.

12. A non-transitory computer-readable storage medium storing a program for causing a computer to execute a control method comprising:
- obtaining designated part information from a storage unit configured to store a plurality of pieces of part information each including an imaging part indicating a part of an object to be imaged and an extraction size of an extraction area on a radiation image;
- recognizing a region of interest from the radiation image based on the imaging part included in the obtained part information; and
- arranging the extraction area with a predetermined extraction size in association with the obtained part information on the radiation image in accordance with the recognized region of interest.

* * * * *